United States Patent
Martin et al.

(10) Patent No.: US 6,603,502 B2
(45) Date of Patent: Aug. 5, 2003

(54) SYSTEM FOR OMNIDIRECTIONAL IMAGE VIEWING AT A REMOTE LOCATION WITHOUT THE TRANSMISSION OF CONTROL SIGNALS TO SELECT VIEWING PARAMETERS

(75) Inventors: H. Lee Martin, Knoxville, TN (US); Daniel P. Kuban, Oak Ridge, TN (US)

(73) Assignee: Internet Pictures Corporation, Oak Ridge, TN (US)

( * ) Notice: Subject to any disclaimer, the term of this patent is extended or adjusted under 35 U.S.C. 154(b) by 0 days.

(21) Appl. No.: 09/259,273

(22) Filed: Mar. 1, 1999

(65) Prior Publication Data

US 2002/0097332 A1 Jul. 25, 2002

Related U.S. Application Data

(63) Continuation of application No. 08/870,410, filed on Jun. 5, 1997, now Pat. No. 5,877,801, which is a continuation of application No. 08/339,663, filed on Nov. 14, 1994, now abandoned, which is a continuation of application No. 08/189,585, filed on Jan. 31, 1994, now Pat. No. 5,384,588, which is a continuation-in-part of application No. 08/014,508, filed on Feb. 8, 1993, now Pat. No. 5,359,363, which is a continuation of application No. 07/699,366, filed on May 13, 1991, now Pat. No. 5,185,667.

(51) Int. Cl.[7] .......................... H04N 7/00; H04N 5/225
(52) U.S. Cl. ................... 348/36; 348/147; 348/207.99; 348/564
(58) Field of Search ........................ 348/36, 37, 552, 348/43, 44, 39, 46, 147, 143, 315, 335, 340, 342, 91, 564, 565, 207.99; 345/346, 121, 341, 355, 357; 382/293; H04N 7/00, 5/225

(56) References Cited

U.S. PATENT DOCUMENTS

| | | |
|---|---|---|
| 4,549,208 A * | 10/1985 | Kamejima et al. .......... 315/371 |
| 4,656,506 A | 4/1987 | Ritchey |
| 4,728,839 A | 3/1988 | Coughlan et al. |
| 4,772,942 A | 9/1988 | Tuck |
| 4,905,077 A * | 2/1990 | Ishii ........................... 348/588 |
| 5,023,725 A | 6/1991 | McCutcheon |
| 5,047,868 A * | 9/1991 | Takeda et al. ............... 386/109 |
| 5,067,019 A | 11/1991 | Juday et al. |
| 5,068,735 A | 11/1991 | Tuchiya et al. |
| 5,130,794 A | 7/1992 | Ritchey |
| 5,185,667 A | 2/1993 | Zimmermann |
| 5,325,483 A * | 6/1994 | Ise et al. ..................... 345/501 |
| 5,444,478 A | 8/1995 | LeLong et al. |
| 5,495,576 A | 2/1996 | Ritchey |
| 5,644,715 A * | 7/1997 | Baugher ..................... 709/228 |
| 6,121,966 A * | 9/2000 | Teodosio et al. ........... 345/346 |

OTHER PUBLICATIONS

Shenchang Eric Chen, et al., "View Interpolation For Image Synthesis", Computer Graphics Proceedings, Annual Conferences Series, Aug. 1–6, 1993, pp. 279–288.

* cited by examiner

Primary Examiner—Michael H. Lee
(74) Attorney, Agent, or Firm—Frost Brown Todd LLC

(57) ABSTRACT

A system for achieving perspective-corrected views at a location removed from the site of the creation of a distorted wide angle image without the transmission of control signals to the site of image creation. Angles of tilt, pan and rotation, as well as degrees of magnification, are achieved without the use of mechanical devices by using transform algorithms. The system provides for the transmission of signals related to an uncorrected image from a site where this distorted image is created, with the transmitted signals being received at one or more processing sites for creating the perspectively-corrected views. Transmission can be via telephone lines, with the system including signal compression and decompression units. Wireless transmission is also utilized where desired.

32 Claims, 3 Drawing Sheets

SYSTEM FOR OMNIDIRECTIONAL IMAGE VIEWING AT A REMOTE LOCATION WITHOUT THE TRANSMISSION OF CONTROL SIGNALS TO SELECT VIEWING PARAMETERS

This is a Continuation application based upon patent application Ser. No. 08/870,410 filed Jun. 5, 1997, now U.S. Pat. No. 5,877,801, which is a Continuation application based upon patent application Ser. No. 08/339,663 filed Nov. 14, 1994, now abandoned, which is a Continuation application based upon patent application Ser. No. 08/189,585 filed Jan. 31, 1994, now U.S. Pat. No. 5,384,588, which is a Continuation-In-Part application based upon patent application Ser. No. 08/014,508 filed Feb. 8, 1993, now U.S. Pat. No. 5,359,363, which is a Continuation application based upon patent application Ser. No. 07/699,366 filed May 13, 1991, now U.S. Re-Issue Pat. No. 32,607 and formerly U.S. Pat. No. 5,185,667.

TECHNICAL FIELD

The present invention relates generally to apparatus for obtaining a wide field of view at a first location without the use of moving parts, and for selecting a portion or portions of that view under selected viewing parameters at a second location without the transmission of control signals from the second location to the first location. Further, the invention relates to the transformation of the selected view into a correct perspective for human viewing at the second location.

BACKGROUND ART

The fundamental apparatus, algorithm and method for achieving perspectively-corrected views of any selected portion of a hemispherical (or other wide angle) field of view are described in detail in the above-cited U.S. Pat. No. 5,185,667. This patent is incorporated herein by reference for its teachings. Through the use of this technology no moving parts are required for achieving pan, tilt and rotation "motions", as well as magnification. Briefly, a wide angle field of view image is captured into an electronic memory buffer. A selected portion of the captured image containing a region of interest is transformed into a perspective correct image by an image processing computer. This provides direct mapping of the wide angle image region of interest into a corrected image using an orthogonal set of transformation algorithms. The viewing orientation, and other viewing perimeters, are designated by a command signal generated by either a human operator or a form of computerized input. The transformed image is deposited in a second electronic memory buffer where it is then manipulated to produce the output image as requested by the command signal.

The invention of that patent was envisioned as being primarily a unitary system in that all components were located in close proximity. Even in the subsequent patent applications (Ser. No. 08/014,508, above-cited, and Ser. No. 08/068,776, filed Jun. 1, 1993) of related technology, the inventions were envisioned as having all components in close proximity. As such, there could be ready verification of operation, alignment and any needed adjustment.

There are applications, however, for the same type of omniviewing of wide angle images where there is a substantial distance between where the initial image occurs and the location where the perspectively-corrected views are to be utilized. For example, in the teleconferencing art some type of display is exhibited at one location, and persons at a distant location desire to view all or a selected portion of the display. According to common practice prior to the development of the basic system for providing a selected image without the use of moving components, control signals had to be sent to the site of the display so as to make necessary adjustments to equipment at that site so as to select a portion of the display, or enhance a selected portion, for use of the view at the distant location. Further, it is often desirable to have a plurality of viewers each individually wishing to observe selected portions of the image, with those plurality of viewers potentially scattered at separate viewing locations. The prior art for this situation would require a plurality of cameras (video sources) and a plurality of control signals being sent to the site of the images, and each viewer taking a selected time for their individual viewing.

Accordingly, it is an object of the present invention to utilize variations on the technology of production of perspective-corrected views, at one or more locations, of at least portions of an overall image occurring at a distant location.

It is another object of the present invention to provide for the generation of a wide angle image at one location and for the transmission of a signal corresponding to that image to another location, with the received transmission being processed so as to provide a perspective-corrected view of any selected portion of that image at the other location.

It is also an object of the present invention is to provide for the generation of a wide angle image at one location and for the transmission of a signal corresponding to that image to another location, with the received transmission being processed so as to provide at a plurality of stations a perspective-corrected view of any selected portion of that image, with each station selecting a desired perspective-corrected view.

A further object of the present invention is to provide for the generation of a wide angle image at one location and for the transmission of a signal corresponding to that image to a plurality of other locations, with the received transmission at each location being processed so as to provide a perspective-corrected view of any selected portion of that image, with the selected portion being selected at each of the plurality of other locations.

These and other objects of the present invention will become apparent upon a consideration of the drawings referred to hereinafter, and the detailed description thereof.

BRIEF SUMMARY OF THE INVENTION

In accordance with the present invention, there is provided a video camera at a first location, with that camera having a wide field of view lens, such as a fish-eye lens, to produce an electrical signal corresponding to the image as seen through the lens. This electrical signal, which is distorted because of the curvature of the lens, is inputted to apparatus for the transmission of the electrical signal to a remote location. The transmission can be by wire or wireless depending upon the circumstances. If by telephone wire, the apparatus for transmission includes a "compression" portion due to the lower band width of these lines. If transmission is to be wireless, appropriate broadcasting apparatus is included.

At each location where viewing is desired, there is apparatus for receiving the transmitted signal. In the case of the telephone line transmission, "decompression" apparatus is included as a portion of the receiver. The received signal is then digitized. A selected portion of the digitized signal, as selected by operator commands, is transformed using the algorithms of the above-cited U.S. Pat. No. 5,185,667 into a perspective-corrected view corresponding to that selected portion. This selection by operator commands includes options of angles of pan, tilt, and rotation, as well as degrees of magnification.

The system provides for alternate types of receiving command signals. For example, there can be a plurality of stations for inputting of these command signals to a single transform unit. Further, there can be the inputting of command signals at each of several receiving stations, each of these receiving stations including a transform unit.

BEST MODE FOR CARRYING OUT THE INVENTION

Figure 1:
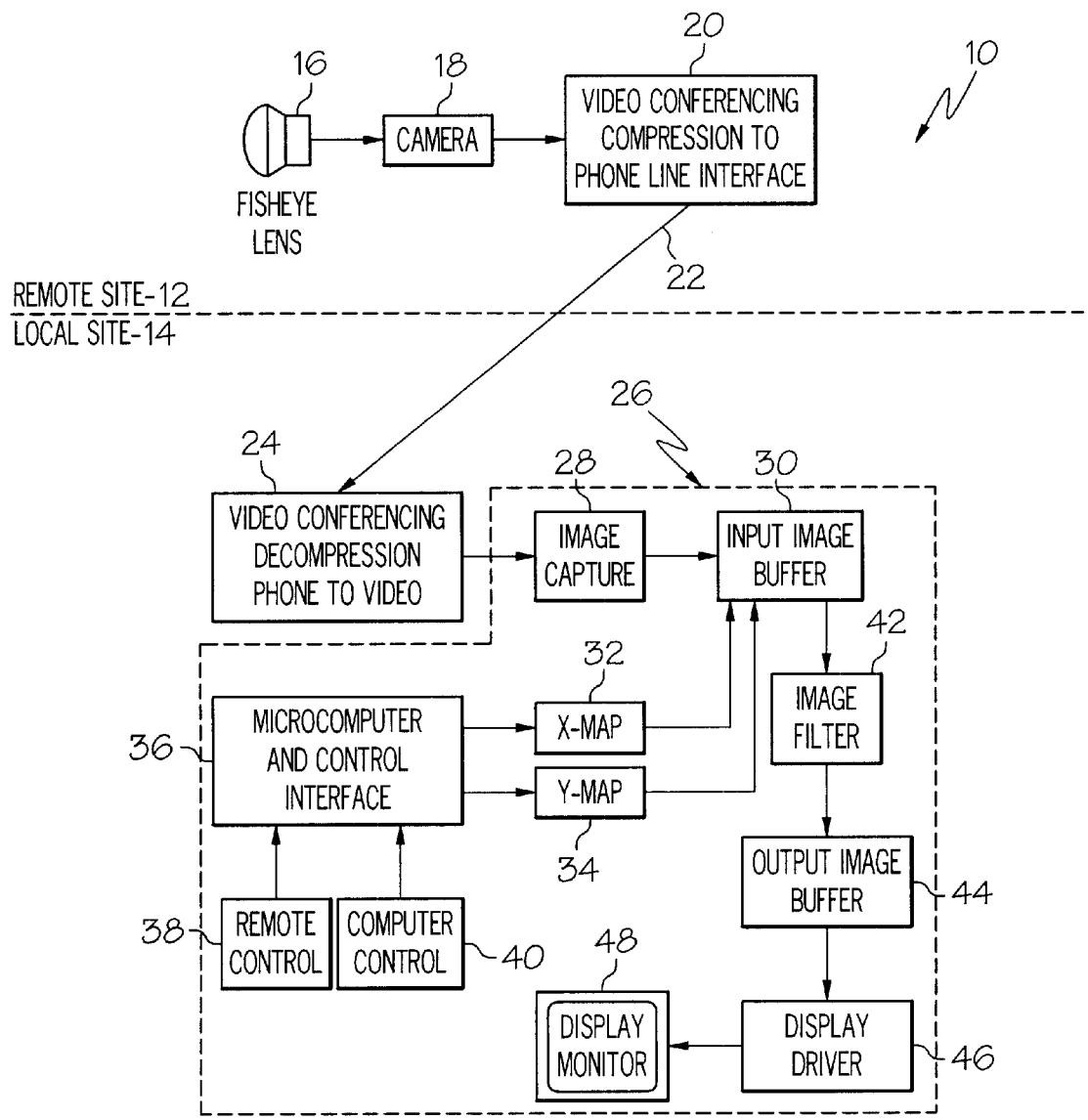
FIG. 1 is a block diagram of one embodiment of the present invention as applied to the transmission of image signals via telephone lines to a signal processing station wherein transformation of a selected portion of a distorted image to a perspective-corrected view is achieved.

One embodiment of the present invention is illustrated generally at 10 of FIG. 1, this embodiment being primarily for use with signal transmission via telephone lines. It will be understood that in this embodiment, as well as others to be described hereinafter, there are two widely separated locations, designated as a "remote site" 12 and a "local site" 14. Situated at the remote site 12 is a wide angle lens 16, such as a "fisheye" lens, and a video camera 18 for converting any image seen by the lens 16 into electrical signals corresponding to that image. Typically the lens is an 8 mm F2.8 lens as manufactured by Nikon, and the camera is a Videk Digital Camera. These signals are inputted to a compression circuit 20, such as that manufactured as Rembrant VP model, manufactured by Compression Labs. Inc. Compression is necessary because telephone lines 22 leading from the remote site 12 to the local site 14 have a lower band width than other methods of signal transfer (see FIGS. 2 and 3). The compressed signal representing the image is then applied to the phone lines 22 for transmission to the local site 14.

At the local site 14 the signals on the phone lines 22 are applied to a decompression circuit 24, such as that manufactured as Rembrant VP model, manufactured by Compression Labs., Inc., this unit being both the compression and decompression. Thus, the signal output of the camera 18 is reconstructed for processing via circuits 26 of the type described in the above-cited U.S. Pat. No. 5,185,667. For example, the reconstructed signal is applied to an image capture circuit 28 such as Texas Instrument's TMS 34061 integrated circuits, to be digitized, and then stored in an input image buffer 30. Typically this buffer (and an output buffer referred to hereinafter) is constructed using Texas Instrument TMS44C251 video random access memory chips or their equivalents.

An image processing system consists of an X-MAP and a Y-MAP processor shown at 32 and 34, respectively. These perform two-dimensional transform mapping of the signals, and are under control by a microcomputer and control interface 36. The transformation achieved by these are described in detail in the above-cited U.S. Pat. No. 5,185,667. The in addition to determining the desired transformation coefficients based on orientation angle, magnification, rotation and light sensitivity. Information as to parameters for these determinations is provided through a user-operated controller 38 and/or a computer controller 40. Typically, the control interface 36 can be accomplished with any of a number of microcontrollers including the Intel 80C196. After the transformation steps, the signal is passed through an image filter 42 to an output image buffer 44. This filter 42, as well as the X-MAP and Y-MAP transform processors utilize application specific integrated circuits (ASICs) or other means as will be known to persons skilled in the art.

From the output image buffer 44 the transformed signals feed a display driver 46 for then being displayed on a monitor 48. The driver 46 typically can be Texas Instruments TMS34061 or the equivalent. Its output is compatible with most commercial television displays.

Figure 2:
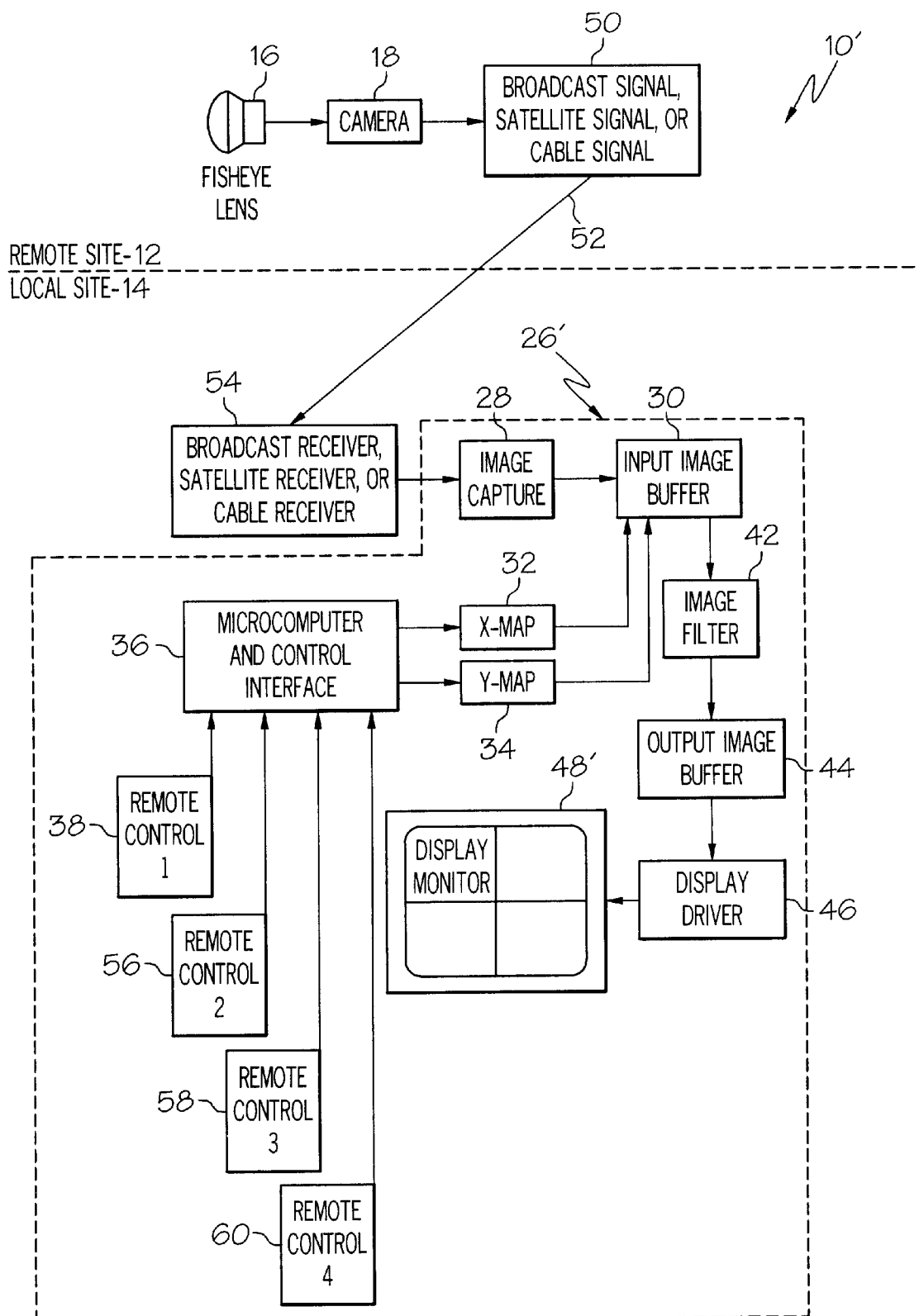
FIG. 2 is a block diagram of another embodiment of the present invention as applied to the transmission of image signals via "broadcast" (radiobroadcast signal, satellite signal, cable signal, etc.) to a signal processing station wherein transformation of selected portions of a distorted image perspective-corrected views is achieved, with the possible input of a plurality of command signals to each select a desired portion of the image for transformation.

Another embodiment of the present invention for generating signals corresponding to a distorted image at one location, and for achieving a perspectively corrected view at another location, is illustrated at 10' in FIG. 2. In this embodiment, the same lens 16 and video camera 18 are utilized as in FIG. 1. However, the electrical signals corresponding to a distorted image are inputted into a signal transmitter 50. This transmitter so can generate a broadcast signal, a satellite signal, a cable signal, a sonar signal, etc. at the remote site 12.

As indicated, the transmitted signals 52 are received in a receiver 54 corresponding to the particular type of signal. Thereafter, the signals representing the distorted image are fed into the processing circuitry 26' similar to that described with regard to FIG. 1. The only differences are the illustration of several remote controller inputs 56, 58, and 60 in addition to the initial controller input 38. While only a total of four input controllers are illustrated, a larger or a smaller number can, of course, be utilized. The other difference of this circuit from that shown in FIG. 1 is that the display monitor 48' is adapted to depict four views as selected by the four input controllers. It will be recognized that a fewer of)a greater number of views can be shown on the display monitor 48'.

Figure 3:
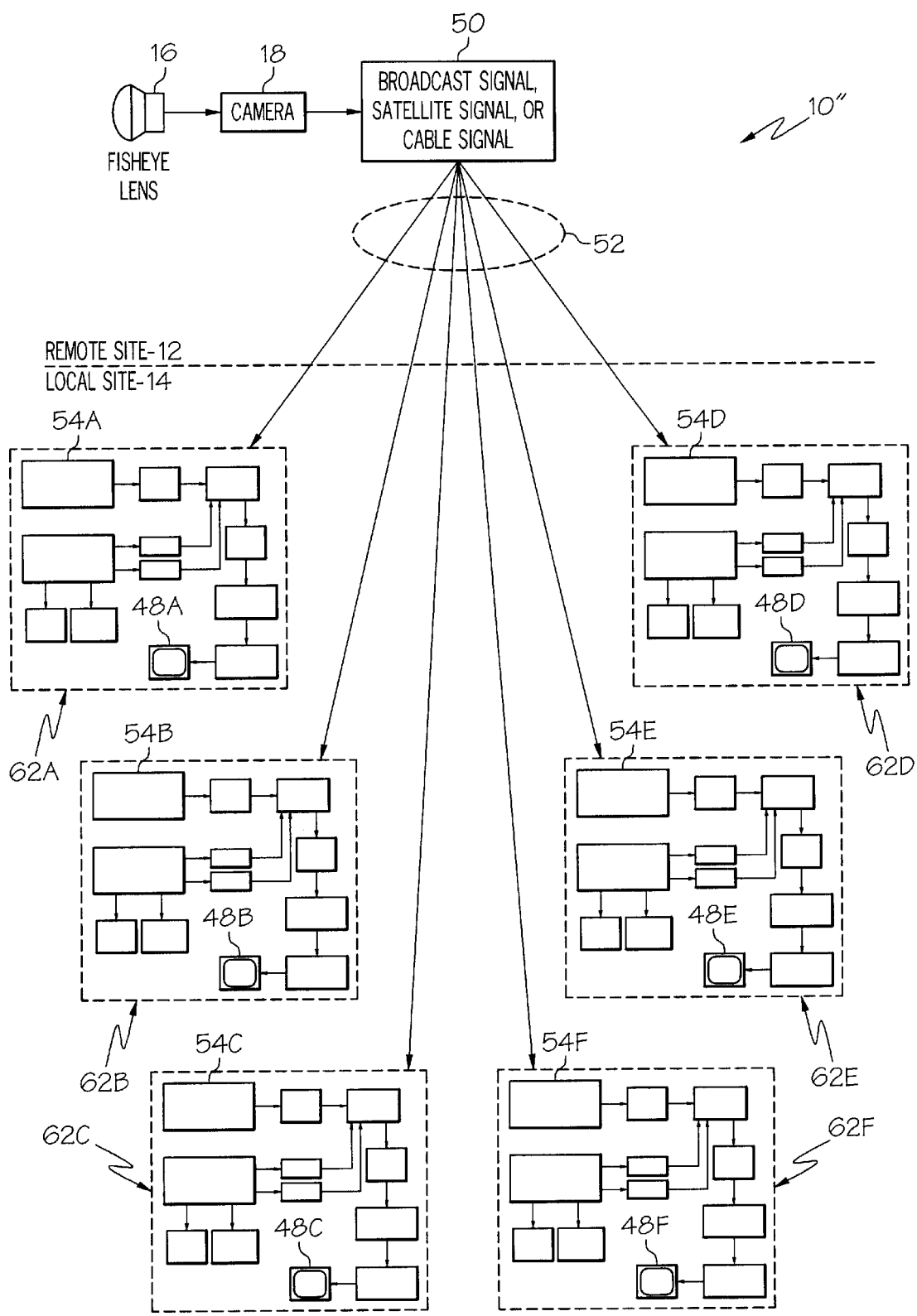
FIG. 3 is a block diagram of a further embodiment of the present invention wherein the distorted image signal is transmitted to a plurality of locations, each of these locations having provision for transformation of selected portions of the image into perspective-corrected views.

A further embodiment of the present invention is illustrated at 10" in FIG. 3. This embodiment illustrates a combination of elements of FIGS. 1 and 2. For example, at the remote site there is a wide angle lens 16 and video camera 18 to produce electrical signals corresponding to a distorted image to a transmitter 50. This transmitter 50 sends the signals 52 to a number of receiving stations designated, for example, at six locations 62A through 62F. Each of these stations has a receiver unit 54A through 54F of the type shown in FIG. 2. All of the other equipment at each station is identical with that of FIG. 2, with only a single view monitor 48A through 48F being illustrated; however, a multi-view monitor 48' can be utilized.

The present invention has the capability to achieve pan and tilt of the image seen by the camera 18 from a local site while the camera is positioned at a remote site. Further, the image can be rotated any number of desired degrees up to 360°. This capability provides the ability to align the vertical image with the gravity vector to maintain a proper perspective in the image display regardless of the pan or tilt angle of the image. The processing system at the local site also supports a change in the magnification (commensurate with a zoom function). These selectable functions, as well as a selection of a desired portion(s) of the image are achieved without sending any control signals to the remote site.

The performance of the transform of a distorted image into a perspectively corrected image, and the selection of the desired viewing parameters, are achieved by programming the microcomputer 36, the X-MAP transform processor 32 and the Y-MAP transform processor 34 based upon the postulates and equations set forth below as contained in the above-cited U.S. Pat. No. 5,185,667.

Postulate 1: Azimuth Angle Invariability

For object points that lie in a content plane that is perpendicular to the image plane and passes through the image plane origin, all such points are mapped as image points onto the line of intersection between the image plane and the content plane, i.e. along a radial line. The azimuth angle of the image points is therefore invariant to elevation and object distance changes within the content plane.

Postulate 2: Equidistant Projection Rule

The radial distance, r, from the image plane origin along the azimuth angle containing the projection of the object point is linearly proportional to the zenith angle $\beta$, where $\beta$ is defined as the angle between a perpendicular line through the image plane origin and the line from the image plane origin to the object point. Thus the relationship:

$$r = k\beta \tag{1}$$

Using these properties and postulates as the foundation of the lens system, the mathematical transformation for obtaining a perspective corrected image can be determined. Coordinates u,v describe object points within the object plane. The coordinates x,y,z describe points within the image coordinate frame of reference.

The object plane is a typical region of interest to determine the mapping relationship onto the image plane to properly correct the object. The direction of view vector, DOV[x,y,z], determines the zenith and azimuth angles for mapping the object plane, UV, onto the image plane, XY. The object plane is defined to be perpendicular to the vector, DOV[x,y,z].

The location of the origin of the object plane in terms of the image plane [x,y,z] in spherical coordinates is given by:

$$x = D \sin \beta \cos \partial$$
$$y = D \sin \beta \sin \partial \tag{2}$$
$$z = D \cos \beta$$

where D=scaler length from the image plane origin to the object plane origin, $\beta$ is the zenith angle, and $\partial$ is the azimuth angle in image plane spherical coordinates. The origin of object plane is represented as a vector using the components given in Equation 1 as:

$$DOV[x,y,z] = [D \sin \beta \cos \partial, D \sin \beta \sin \partial, D \cos \beta] \tag{3}$$

DOV[x,y,z] is perpendicular to the object plane and its scaler magnitude D provides the distance to the object plane. By aligning the YZ plane with the direction of action of DOV[x,y,z], the azimuth angle $\partial$ becomes either 90 or 270 degrees and therefore the x component becomes zero resulting in the DOV[x,y,z] coordinates:

$$DOV[x,y,z] = [0, -D \sin \beta, D \cos \beta] \tag{4}$$

The object point relative to the UV plane origin in coordinates relative to the origin of the image plane is given by the following:

$$x = u$$
$$y = v \cos \beta \tag{5}$$
$$z = v \sin \beta$$

therefore, the coordinates of a point P(u,v) that lies in the object plane can be represented as a vector P[x,y,z] in image plane coordinates:

$$P[x,y,z] = [u, v \cos \beta, v \sin \beta] \tag{6}$$

where P[x,y,z] describes the position of the object point in image coordinates relative to the origin of the UV plane. The object vector O[x,y,z] that describes the object point in image coordinates is then given by:

$$O[x,y,z] = DOV[x,y,z] + P[x,y,z] \tag{7}$$

$$O[x,y,z] = [u, v \cos \beta - D \sin \beta, v \sin \beta + D \cos \beta] \tag{8}$$

Projection onto a hemisphere of radius R attached to the image plane is determined by scaling the object vector O[tx,y,z] to produce a surface vector S[x,y,z]:

$$S[x, y, z] = \frac{RO(x, y, z)}{|O[x, y, z]|} \tag{9}$$

By substituting for the components of O[x,y,z] from Equation 8, the vector S[x,y,z] describing the image point mapping onto the hemisphere becomes:

$$S[x, y, z] = \frac{RO[u, (v\cos\beta - D\sin\beta), (v\sin\beta + D\cos\beta)]}{\sqrt{u^2 + (v\cos\beta - D\sin\beta)^2 + (v\sin\beta + D\cos\beta)^2}} \tag{10}$$

The denominator in Equation 10 represents the length or absolute value of the vector O[x,y,z] and can be simplified through algebraic and trigonometric manipulation to give:

$$S[x, y, z] = \frac{RO[u, (v\cos\beta - D\sin\beta), (v\sin\beta + D\cos\beta)]}{\sqrt{u^2 + v^2 + D^2}} \tag{11}$$

From Equation 11, the mapping onto the two-dimensional image plane can be obtained for both x and y as:

$$x = \frac{Ru}{\sqrt{u^2 + v^2 + D^2}} \tag{12}$$

$$y = \frac{R(v\cos\beta - D\sin\beta)}{\sqrt{u^2 + v^2 + D^2}} \tag{13}$$

Additionally, the image plane center to object plane distance D can be represented in terms of the image circular radius R by the relation:

$$D = mR \tag{14}$$

where m represents the scale factor in radial units R from the image plane origin to the object plane origin.

Substituting Equation 14 into Equations 12 and 13 provides a means for obtaining an effective scaling operation or magnification which can be used to provide zoom operation.

$$x = \frac{Ru}{\sqrt{u^2 + v^2 + m^2 R^2}} \quad (15)$$

$$y = \frac{R(v\cos\beta - mR\sin\beta)}{\sqrt{u^2 + v^2 + m^2 R^2}} \quad (16)$$

Using the equations for two-dimensional rotation of axes for both the UV object plane and the XY image plane the last two equations can be further manipulated to provide a more general set of equations that provides for rotation within the image plane and rotation within the object plane.

$$x = \frac{R[uA - vB + mR\sin\beta\sin\partial]}{\sqrt{u^2 + v^2 + m^2 R^2}} \quad (17)$$

$$y = \frac{R[uC - vD + mR\sin\beta\cos\partial]}{\sqrt{u^2 + v^2 + m^2 R^2}} \quad (18)$$

where:

$A = (\cos\emptyset \cos\partial - \sin\emptyset \sin\partial \cos\beta)$ $B = (\sin\emptyset \cos\partial + \cos\emptyset \sin\partial \cos\beta)$ $C = (\cos\uparrow \sin\partial + \sin\emptyset \cos\partial \cos\beta)$ (19)

$D = (\sin\emptyset \sin\partial - \cos\emptyset \cos\partial \cos\beta)$ and where:

$R$ = radius of the image circle $\beta$ = zenith angle $\partial$ = Azimuth angle in image plane $\emptyset$ = Object plane rotation angle $m$ = Magnification $u, v$ = object plane coordinates $x, y$ = image plane coordinates The Equations 17 and 18 provide a direct mapping from the UV space to the XY image space and are the fundamental mathematical result that supports the functioning of the present omnidirectional viewing system with no moving parts. By knowing the desired zenith, azimuth, and object plane rotation angles and the magnification, the locations of x and y in the imaging array can be determined. This approach provides a means to transform an image from the input video buffer 30 to the output video buffer 44 exactly. Also, the image system is completely symmetrical about the zenith, therefore, the vector assignments and resulting signs of various components can be chosen differently depending on the desired orientation of the object plane with respect to the image plane. In addition, these postulates and mathematical equations can be modified for various lens elements as necessary for the desired field-of-view coverage in a given application.

The input means defines the zenith angle, $\beta$, the azimuth angle, $\partial$, the object rotation, $\emptyset$, and the magnification, m. These values are substituted into Equations 19 to determine values for substitution into Equations 17 and 18. The image circle radius, R, is a fixed value that is determined by the camera lens and element relationship. The variables u and v vary throughout the object plane determining the values for x and y in the image plane coordinates.

From the foregoing it will be understood by persons skilled in the art that the art of the omniview motionless camera system has been extended for applications such as teleconferencing where information displayed at one location can be transmitted to a second location, with complete control of the selection of viewing parameters being made at that second site without any control being transmitted to the first site. This permits a multi-station receipt of the information and control at each station.

Although certain citations to commercially available equipment are made herein, there is no intent to limit the invention by these citations. Rather, any limitation of the is present invention is by the appended claims and their equivalents.

We claim:

1. A method of controlling an image display, said method comprising:

receiving at least one digital video signal corresponding to a captured wide-angle video image, said wide-angle video image having a field of view and being distorted relative to human perception;

selecting two or more views within the wide-angle field of view;

processing the digital video signal to create two or more perspective-corrected video images each corresponding to one of the selected views; and displaying the perspective-corrected video images simultaneously on the same display monitor.

2. The method of claim 1, wherein the wide-angle video image is captured with a fisheye lens.

3. The method of claim 1, wherein the captured wide-angle video image comprises a substantially circular image.

4. The method of claim 1, wherein the wide-angle field of view is hemispherical.

5. The method of claim 1, further comprising the step of storing the received digital video signal.

6. The method of claim 1, wherein the digital video signal is compressed.

7. The method of claim 6, wherein the step of receiving the digital video signal is executed via a telephone line.

8. The method of claim 7, further comprising the step of decompressing the digital video signal.

9. The method of claim 6, further comprising the step of storing the compressed digital video signal.

10. A digital video signal for viewing using the method of claim 1.

11. The method of claim 1, wherein the step of processing includes multi-dimensional transform mapping of the digital video signal.

12. The method of claim 11, wherein said multi-dimensional transform mapping is performed by a microprocessor and an associated control interface that are controlled by a user-operated controller indicating a transformation specification for at least one of orientation angle, magnification and rotation.

13. The method of claim 12, wherein the user-operated controller includes at least one of a computer keyboard, a computer mouse, a toggle switch and a joystick.

14. The method of claim 1, wherein the step of selecting comprises selecting four different views within the wide-angle field of view.

15. The method of claim 14, wherein the step of processing comprises creating four perspective-corrected video images each corresponding to one of four selected views.

16. The method of claim 15, wherein the step of displaying comprises displaying each of the four perspective-corrected video images in a different quadrant of the monitor.

17. A computer-readable medium having instructions for controlling an image display, said instructions comprising:

receiving at least one signal corresponding to a captured wide-angle digital image output from a digital imaging system;

processing two or more selected perspective-corrected portions of the received captured wide-angle digital image; and simultaneously displaying on the same monitor said two or more selected perspective-corrected portions.

18. The computer-readable medium of claim 17, wherein the captured wide-angle digital image is rotatable up to 360°.

19. The computer-readable medium of claim 17, wherein the captured wide-angle digital image comprises a substantially circular image.

20. The computer-readable medium of claim 17, wherein the captured wide-angle digital image comprises a substantially hemispherical image.

21. The computer-readable medium of claim 17, wherein said processing the selected perspective-corrected portion of the received captured wide-angle digital image includes storing the selected perspective-corrected portion of the received captured wide-angle digital image.

22. The computer-readable medium of claim 17, further comprising compressing the captured wide-angle digital image output from the digital imaging system.

23. The computer-readable medium of claim 22, wherein said receiving the captured wide-angle digital image is executed via a telephone line.

24. The computer-readable medium of claim 23, further comprising decompressing captured wide-angle digital image.

25. The computer-readable medium of claim 22, further comprising storing the compressed captured wide-angle digital image.

26. The computer-readable medium of claim 24, further comprising image processing the decompressed captured wide-angle digital image.

27. The computer-readable medium of claim 26, wherein said image processing includes multi-dimensional transform mapping the decompressed captured wide angle-digital image.

28. The computer-readable medium of claim 27, wherein said multi-dimensional transform mapping is controlled by a user-operated controller indicating a transformation specification for at least one of orientation angle, magnification and rotation.

29. The computer-readable medium of claim 28, wherein the user-operated controller includes at least one of a computer keyboard, a computer mouse, a toggle switch and a joystick.

30. A video conference system comprising the computer readable medium of claim 17.

31. The computer-readable medium of claim 17, wherein the two or more selected perspective-corrected portions are each a different view within the captured wide-angle digital image in multiple views.

32. The computer-readable medium of claim 31, wherein the step of displaying comprises displaying each selected perspective-corrected portion on a quadrant of the monitor.

* * * * *

UNITED STATES PATENT AND TRADEMARK OFFICE
CERTIFICATE OF CORRECTION

PATENT NO.     : 6,603,502 B2
DATED          : August 5, 2003
INVENTOR(S)    : Martin et al.

It is certified that error appears in the above-identified patent and that said Letters Patent is hereby corrected as shown below:

<u>Title page, Item [54] and Column 1, lines 1-5,</u>
Title should read -- SIMULTANEOUS DISPLAY OF MULTIPLE VIEWS IN WIDE ANGLE VIDEO --.

Signed and Sealed this

Eighteenth Day of November, 2003

JAMES E. ROGAN
*Director of the United States Patent and Trademark Office*